United States Patent
Roy et al.

(10) Patent No.: US 6,743,243 B1
(45) Date of Patent: Jun. 1, 2004

(54) SUPPORT DEVICE FOR ENDOSCOPIC SUTURLESS ANASTOMOSIS

(76) Inventors: Sumit Roy, Industrigt. 71A, N-0357 Oslo (NO); Erik Fosse, Maridalsvn. 71B, N-0458 Oslo (NO)

( * ) Notice: Subject to any disclaimer, the term of this patent is extended or adjusted under 35 U.S.C. 154(b) by 0 days.

(21) Appl. No.: 09/623,496
(22) PCT Filed: Mar. 19, 1999
(86) PCT No.: PCT/NO99/00093
§ 371 (c)(1), (2), (4) Date: Nov. 20, 2000
(87) PCT Pub. No.: WO99/48427
PCT Pub. Date: Sep. 30, 1999

(30) Foreign Application Priority Data

Mar. 20, 1998 (NO) .......................... 19981277

(51) Int. Cl.⁷ ............................... A61B 17/11
(52) U.S. Cl. ................... 606/153; 606/155; 606/213
(58) Field of Search ................. 606/151, 153, 606/155, 213, 215; 623/1.1

(56) References Cited

U.S. PATENT DOCUMENTS

| | | | |
|---|---|---|---|
| 2,127,903 A | 8/1938 | Bowen | 128/334 |
| 2,453,056 A | 11/1948 | Zack | 128/334 |
| 3,254,650 A | 6/1966 | Collito | 128/334 |
| 3,683,926 A | 8/1972 | Suzuki | 128/334 |
| 4,917,087 A | 4/1990 | Walsh et al. | 606/153 |
| 5,254,113 A | 10/1993 | Wilk | 606/8 |
| 5,540,701 A | 7/1996 | Sharkey et al. | 606/153 |
| 5,643,340 A * | 7/1997 | Nunokawa | 623/1.49 |
| 5,893,886 A | 4/1999 | Zegdi et al. | 623/1 |
| 6,251,116 B1 * | 6/2001 | Shennib et al. | 606/155 |
| 6,395,015 B1 * | 5/2002 | Borst et al. | 606/213 |
| 2002/0116016 A1 * | 8/2002 | Barath | 606/153 |
| 2003/0065343 A1 * | 4/2003 | Yencho et al. | 606/153 |

FOREIGN PATENT DOCUMENTS

| | | |
|---|---|---|
| EP | 0781528 A2 | 7/1997 |
| EP | 0824012 A1 | 2/1998 |
| FR | 1518083 | 3/1967 |
| GB | 1413191 | 11/1975 |
| WO | WO94/27506 | 12/1994 |
| WO | WO97/12555 | 4/1997 |
| WO | WO97/27898 | 8/1997 |
| WO | WO97/47261 | 12/1997 |
| WO | WO98/52474 | 11/1998 |

* cited by examiner

*Primary Examiner*—Henry Bennett
*Assistant Examiner*—Kathryn Odland
(74) *Attorney, Agent, or Firm*—Jacobson Holman PLLC

(57) ABSTRACT

A support device for endoscopic suturless anastomosis between tubular organs include at least a first tubular member provided with a longitudinal slit which permits introduction of the organs to be anastomosed in the device and additional second tubular members in physical continuity with the first tubular member through an opening on the first tubular member. The size of the opening is substantially equal to the luminal area of the second member. The inner and outer diameters of any radial cross section of the second members are constant along its length. The device allows apposition of the two tubular organs to be anastomosed in a variety of spatial patterns and their fixation to each other without sutures or clips, either manually or via remote control, and the creation of luminal continuity between them.

12 Claims, 23 Drawing Sheets

Inflow vessel

Inflow vessel

Outflow vessel

Inflow vessel — Outflow vessel

Inflow vessel   Outflow vessel

Inflow vessel   Outflow vessel

Inflow vessel          Outflow vessel

SUPPORT DEVICE FOR ENDOSCOPIC SUTURLESS ANASTOMOSIS

The present invention relates to a support device for use in suturless anastomosis procedures, and a method for performing suturless anastomosis. The method according to the invention will be referred to in the present specification as IKF-IS technique (Institutt for Kirurgisk Forskning-Intervensjonssenteret).

The risk inherent in the performance of conventional cardiopulmonary bypass grafting (CABG) and the relatively frequent need for reintervention after percutaneous transluminal coronary angioplasty (PTCA) have caused a rising interest in developing thoracoscopy assisted procedures that combine the patient-friendly nature of PTCA with the durable benefits offered by CABG.

Three approaches are currently undergoing evaluation, none of which eliminate the need for both cardiopulmonary bypass and thoracotomy. As these two procedures represent the primary causes of morbidity after CABG, there is an urgent need for developing a minimally invasive procedure that can be performed on a beating heart, entirely under endoscopic-fluoroscopic guidance.

The IKF-IS technique has been envisaged to meet this need.

An important feature of this technique is that its use is not limited to the coronary arteries. An IKF-IS anastomosis can be done in any vascular area within reach of an endoscope. The range of use includes also extravascular tubular structures such as the esophagus, intestines, ureter, biliary ducts and fallopian tubes.

Suturless anastomosis of vessels is not a new concept. A large number of anastomosis devices has been described in literature, though few of them have passed the test of time.

Structurally sound anastomosis between vessels can be rapidly established simply by apposing the vessel ends with interlocking external collars.

GB-B-1.413.191 describes a device for the eversion of hollow organs and a vascular stapling instrument incorporating same. The device optionally comprises a rigid bush with a longitudinal slot or a rigid split bush comprising two pivotally connected half-bushes which can be mechanically disengaged from each other. The bush forms an integral part of an instrument used to evert the cut edges of the limbs of the tubular organ to be anastomosed and temporarily approximate them so as to facilitate suturing or placement of clips that will hold the edges together. When the clips are in place, the instrument and the bush are removed. Thus the device simply acts as an aid to the creation of an anastomosis and in no way removes the drawbacks to using sutures and clips for creating anastomoses.

U.S. Pat. No. 4,917,087 describes devices, kits and methods for non-suture end-to-end and end-to-side anastomosis that employ tubular connection members having clip retaining elements and spring clips which comprise a ring-shaped body with separable opposed ends whereby a circular opening defined by the body can be enlarged.

Unfortunately, these anastomosis devices and others available today were designed for use at open surgery and are not appropriate for endoscopic placement.

EP-A-781.528 describes a fastener for connecting severed blood vessels. The device has a plurality of miniature barbs which pierce the wall of the blood vessel and anchor the fastener in place. In one embodiment the fastener comprises a sheet provided on one of its surfaces with a plurality of barbs, the sheet can be rolled to a diameter smaller than that of the blood vessel, inserted into the blood vessel and unrolled so that the barbs pierce and anchor in the inner wall of the blood vessel. The sheet can alternatively be wrapped round the blood vessel so that the barbs pierce and anchor to the outer wall of the blood vessel. The bond strength of the device as tested is not adequate for clinical use, because the biologic response is not appropriate or the design does not provide the structural strength to tolerate the expected loading forces (whether in shear or in tension is not specified in the document) at the interface between the device and the vessel surface. The penetration of the vessel wall by the barbs on the device can cause separation of the layers of the vessel wall, which in turn can lead to thrombus formation or dissection at the site. The damage to the vessel wall would logically be even more severe if the size of the barbs is increased. Barbs which spontaneously retract, will leave behind holes in the vessel wall from which bleeding could occur. From the description provided in claims 1 and 2, it does not seem possible that these embodiments of the device lend themselves to use via an endoscope. Besides, it is unclear how the barbs will be prevented from inadvertently engaging the adjacent overlying layer as the device is being unfolded by the balloon.

Furthermore WO 98/52474, WO 94/27506, demonstrate devices for performing anastomosis, with and without eversion of the blood vessel respectively, while U.S. Pat. No. 5,254,113 describes the use of strips for anastomosis of intestines. None of these publications do, however, describe a sleeve and use of a sleeve to evert the blood vessels, use of a transitional temperature range (TTR) material in an anastomosis device and an anastomosis device provided with metal collars. In addition, the use of these devices involves the retention of an intraluminal foreign body after anastomosis creation in direct contradiction to the invention in the present application.

FR-A-1.518.083 describes a device for performing end to end and end to side anastomosis. In the embodiment adapted for end to side anastomosis, the device comprises a curved plate with a bore and a joint surrounding the bore. The plate is glued to a first vessel, a hole is cut in said vessel corresponding to said bore in the plate, and a muff containing the second vessel is attached to the joint. The curved plate simply provides a surface area for the adhesive used to attach the joint to the first vessel. Said plate does not permit fastening to the first vessel solely by mechanical means without an adhesive. It does not offer any self-attaching capability. Hence, in case of adhesive failure during the healing process, the curved plate will get dislodged with possibly catastrophic consequences.

An alternative method that has recently been successfully used for coronary artery bypass grafting on a beating heart is the Tulleken technique. By the incorporation of excimer laser arteriotomy, this technique permits the creation of end-to-end bypass without interrupting flow in the diseased vessel. However at its present stage of development, performance of a Tulleken anastomosis via an endoscope is not feasible. The high costs related to the use of excimer lasers further restrict the benefits of the Tulleken technique from the perspective of minimally invasive coronary artery surgery.

The object of the present invention is therefore to provide a device that permits creation of a suturless anastomosis between vessels via an endoscope. This object is achieved by means of a device comprising at least one tubular member, and characterized in that the tubular member is provided with a longitudinal slit, which slit permits introduction of the anastomosed vessels in the device, and the device is adapted for attachment to the vessel without any damage to the vessels' walls.

The need for suturing is entirely eliminated by the invention, reducing danger of vascular trauma.

The anastomosis is exteiiiuy supported by the device according to the invention, this reduces the risk of acute structural failure, delayed aneurysm formation and in the presence of compliance mismatch, improves the long-term patency rate.

The invention will be explained in more detail with the help of the following drawings, where:

FIGS. 21–24A and 24B illustrate an externally stented end-to-side anastomosis by means of the device according to the invention for outflow vessels which can be circumferentially dissected;

FIGS. 33–37A and 37B illustrate an externally stented end-to-side anastomosis by means of the device according to the invention.

FIGS. 38–39A and 39B illustrate an externally stented end-to-side anastomosis by means of the device according to the invention.

Figure 1:
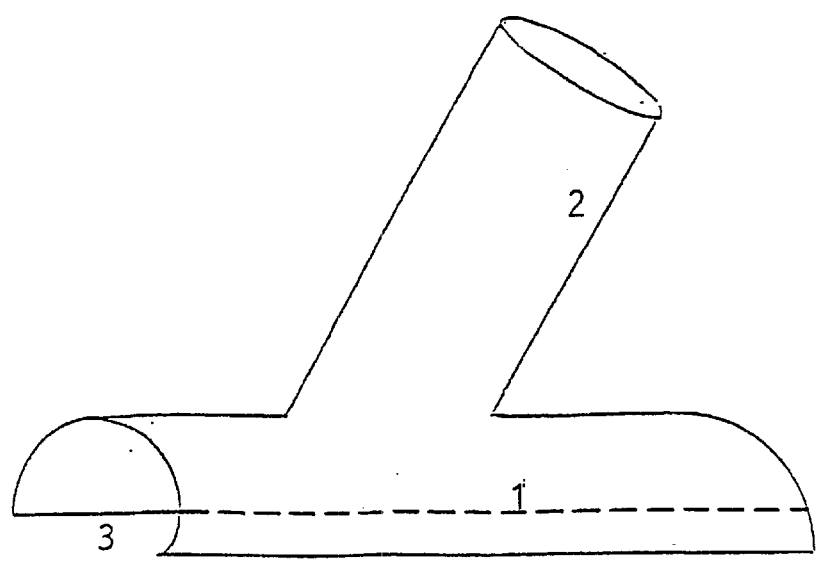
FIGS. 1 and 2 show first (Type Ia) and second (Type Ib) embodiments of the invention for performing end-to-side anastomosis.

FIG. 1 shows a first embodiment of the invention to be used if circumferential dissection of the outflow vessel is not possible (e.g. in coronary artery bypass). This embodiment of the invention shows a first tubular member 1 and a second tubular member 2, where the first tubular member 1 is provided with a longitudinal slit 3. The slit 3 is wide and the edges are not in contact. This characteristic allows use of this embodiment of the invention in cases where the outflow vessel cannot be circumferentially dissected, by placing the first tubular member as a "cap" on the vessel. The second tubular member 2 is attached on the side of the first tubular member 1 opposite the slit. In this embodiment of the invention, the second tubular member does not show a slit.

Figure 2:
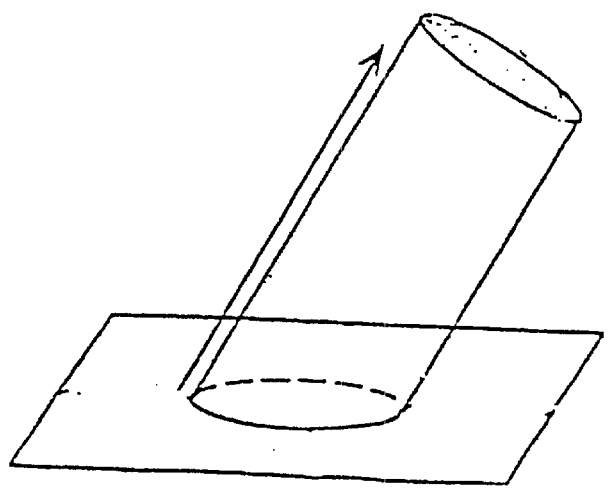

FIG. 2 shows a second embodiment in which the first member is a flat sheet.

Figure 3:
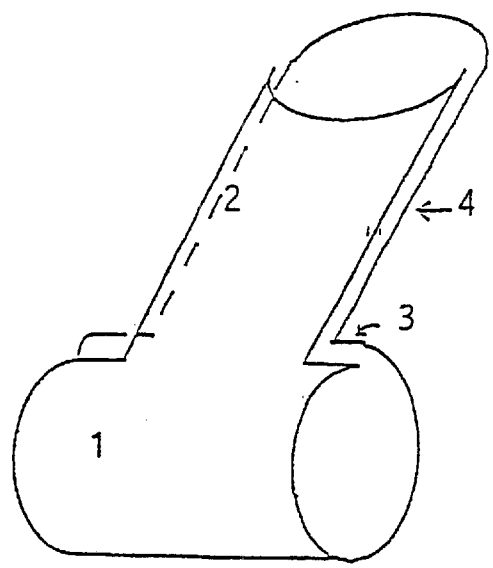
FIG. 3 shows a third (Type II) embodiment of the invention for performing end-to-side anastomosis.

FIG. 3 shows a third embodiment of the invention to be used if circumferential dissection of the outflow vessel is possible. This embodiment of the invention is similar to the embodiment in FIG. 1 except that the second tubular member 2 is split too and it is attached to the first tubular member 1 in such a way that both slits are in contact. The whole device is "hinged" round a longitudinal line in tubular member 1 lying opposite to the slit 3. The term "hinged" in this case is to be understood as a minimum separation of the slit's 3 edges, that otherwise are in contact.

Figure 4:
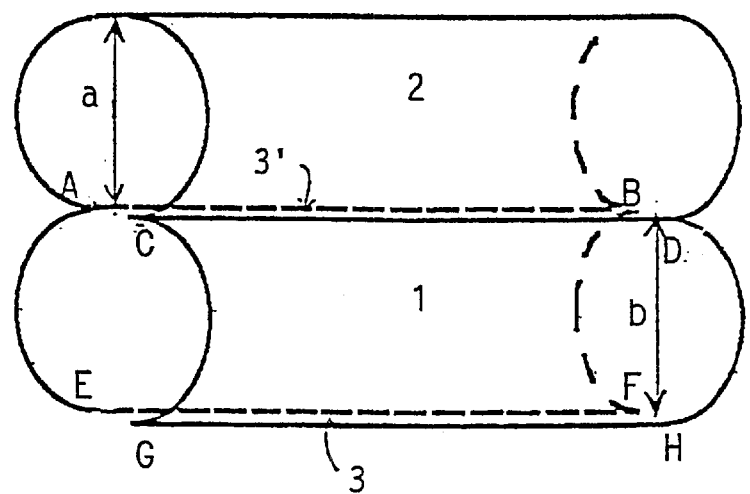
FIG. 4 shows a fourth (Type III) embodiment of the invention for performing end-to-side anastomosis.

FIG. 4 shows a fourth embodiment of the invention adapted for performing end-to-side anastomosis, and where the tubular members 1 and 2 are parallel, and have slits 3 and 3' respectively the tubular members 1 and 2 can have different diameters (a,b) depending on the size of the vessel to be anastomosed. Slit 3' is a longitudinal slit along the common central plane of the device. The two halves of members 1 and 2 can be distracted perpendicular to the longitudinal axis without plastic deformation. Edges AB and CD are not in contact, the distance between them will vary according to the diameters of members 1 and 2. In an embodiment adapted for use with outflow vessels that cannot be circumferentially dissected, edges EF and GH are not in contact. In another embodiment for use with outflow vessels that can be circumferentially dissected edges EF and GH are in contact or overlap each other.

Figure 5:
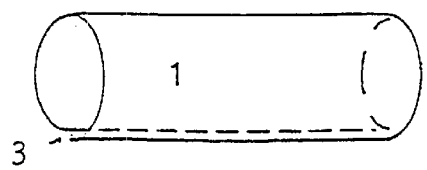
FIG. 5 shows a fifth embodiment of the invention for performing end-to-end anastomosis.

FIG. 5 shows another embodiment of the invention, adapted for performing end-to-end anastomosis. This embodiment comprises only one tubular member 1, with a slit 3.

Figure 6A:
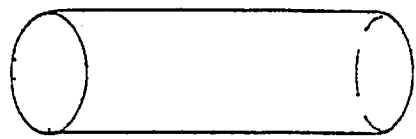
FIGS. 6A and 6B show sixth and seventh embodiments of the invention for performing end-to-side anastomosis.
Figure 6B:

FIGS. 6A and 6B show two embodiments of the inner sleeve of the IKS-IF anatomosis kit for performing end-to-side anastomosis. The embodiment comprises one tubular member without a slit with (FIG. 6A) or without (FIG. 6B) parallel edges.

Figure 7A:
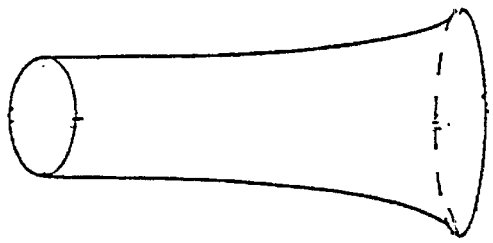
FIGS. 7A and 7B show eigth and ninth embodiments of the invention for performing end-to-side anastomosis.
Figure 7B:
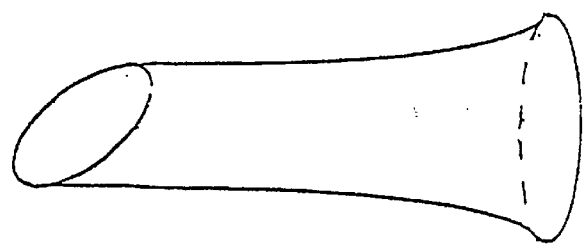

FIGS. 7A and 7B show two embodiments of the fixation sleeve of the IKS-IF anatomosis kit for performing end-to-side anastomosis. The embodiment comprises one funnel shaped tubular member without a slit with (FIG. 7A) or without (FIG. 7B) parallel edges.

Several possibilities are envisaged for the slits' edge area, with the intention of giving the invention high flexibility in use.

Figure 8:
FIG. 8 shows a cross-section of a first alternative joint of the slit's edges.

In one alternative embodiment, the opposing edges of the slit are configured so that they mechanically lock on the application of a centripetal radial force. One possible configuration for this purpose is shown in FIG. 8, where the edges show a Z-profile.

Figure 9:
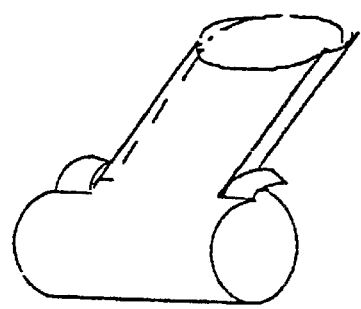
FIG. 9 shows a cross-section of a second alternative joint of the slit's edges.

FIG. 9 shows another possibility for connection of the slit's edges. This possibility consists in extending the slit's edges to form overlapping flaps. The surfaces of the flaps facing each other can be provided with a fastening material, e.g. Velcro strips.

Figure 10:
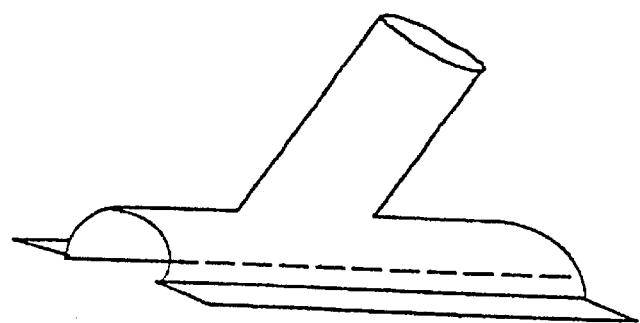
FIG. 10 shows a third alternative of the slit's edges.

FIG. 10 shows an alternative embodiment of linear free edges of the slit member of the anastomosis device type Ia illustrated in FIG. 1.

Figure 11:
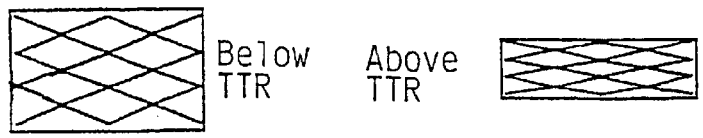
FIG. 11 shows a first alternative embodiment of the fixation sleeve.

FIG. 11 shows an alternative embodiment of the fixation sleeve. The cylindrical segment of the fixation sleeve is reinforced with a cylindrical mesh of a thermodynamic shape-memory metal (e.g. equiatomic nickel-titanium intermetallic compound such as nitinol) with transitional temperature range (TTR) slightly above normal body temperature. Below the TTR, the mesh is in martensitic state and its diameter greater than that of the inner sleeve to simplify placement. Above TTR the metal moves into austenitic state and the cylinder shrinks in diameter to match the inner sleeve.

Figure 12:
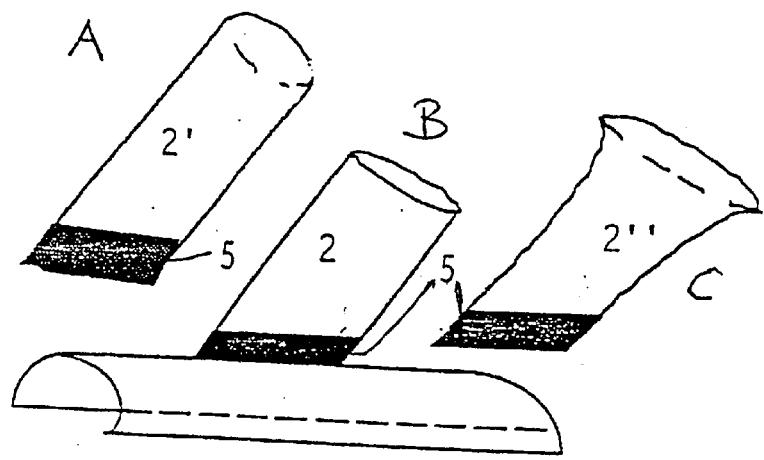
FIGS. 12A, 12B and 12C show second alternative embodiment of the fixation sleeve, and an alternative embodiment of the inner collar and of the anastomosis device.
Figure 36:
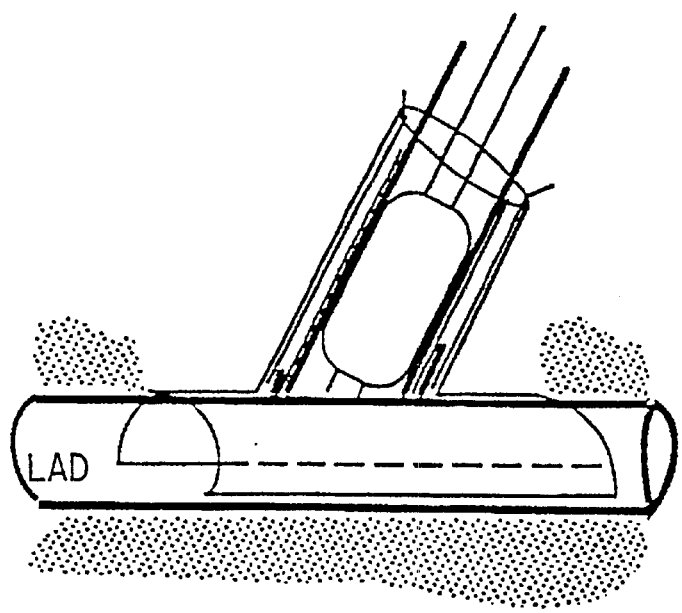

FIGS. 12A, 12B and 12C illustrate alternative embodiment of the fixation (2") and inner (2') sleeves and anastomosis device Ia. Metal collars 5 are embedded in tubular member 2 of anastomosis device type Ia at its junction with tubular member 1, and in the corresponding edges of the inner collar (5') and the fixation collar (5"). After the inner sleeve is mated to the fixation sleeve and the latter to tubular member 2 of anastomosis device Ia (as illustrated in FIG. 36), the collars are crimped together so that inner and fixation sleeves with the tubular organ sandwiched between them is secured to tubular member 2 of the anastomosis device.

In a further embodiment of the anastomosis devices, a continuous wire/strip of a thermodynamic shape-memory metal (e.g. equiatomic nickel-titanium intermetallic compound such as nitinol) with transitional temperature range (TTR) slightly above normal body temperature is embedded along the free edge of the anastomosis device. Below the TTR, the wire frame is in martensitic state and hence malleable so that the device can be straightened, if necessary, to simplify placement. Above TTR the metal moves into austenitic state and the wire regains the shape in its memory, and the anastomosis device recovers its original configuration.

In another embodiment of the invention, the outer surface of the fixation sleeve and inner surface of the side-arm of anastomosis device type II have ridges and troughs respectively (or vice versa) that engage when the side-arm is closed around the fixation sleeve.

In yet another embodiment of the invention, the inner surfaces of the anastomosis device and fixation sleeve and both surfaces of the inner sleeve are lined with an appropriate adhesive.

In yet another embodiment of the invention, the inner surfaces of the anastomosis device and inner sleeve are lined with appropriate pharmacologic agents.

In another embodiment of the invention, the anastomosis device will be reinforced with a mobile, coaxial, close-fitting collar that will be drawn over the device to secure its closure.

It will be clear that any of the above mentioned embodiments can be used together with any embodiment of the invention.

The invention will now be illustrated by way of examples of creation of an anastomosis. These examples are only illustrative and do not in any way limit the scope of the invention as set forth in the attached patent claims.

EXAMPLE 1

Externally Stented End-to-side Anastomosis with an Anastomosis Device (Type I or II [Y-shaped]) (FIGS. 1–3) Alone, for Outflow Vessels Which Cannot be Circumferentially Dissected (e.g. Left Anterior Descending Artery)

Figure 13:
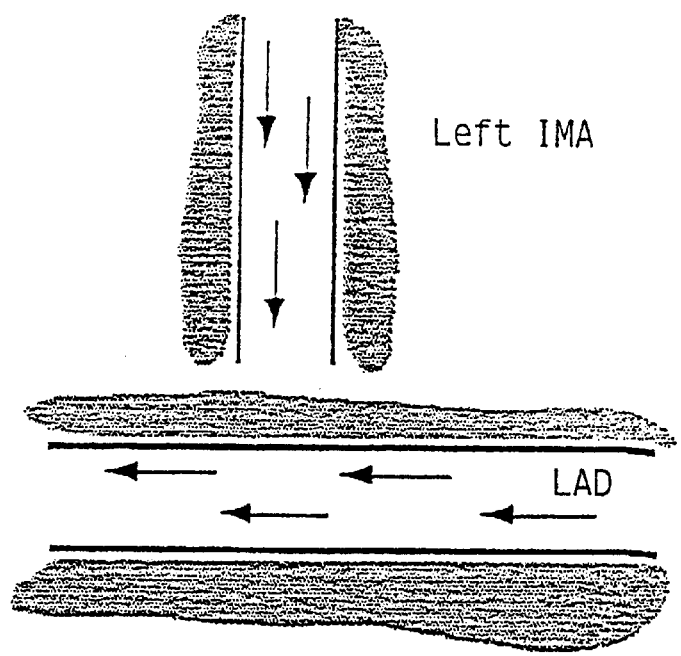
FIGS. 13–20 illustrate an externally stented end-to-side anastomosis by means of the device according to the invention for outflow vessels that cannot be circumferentially dissected.
Figure 14:
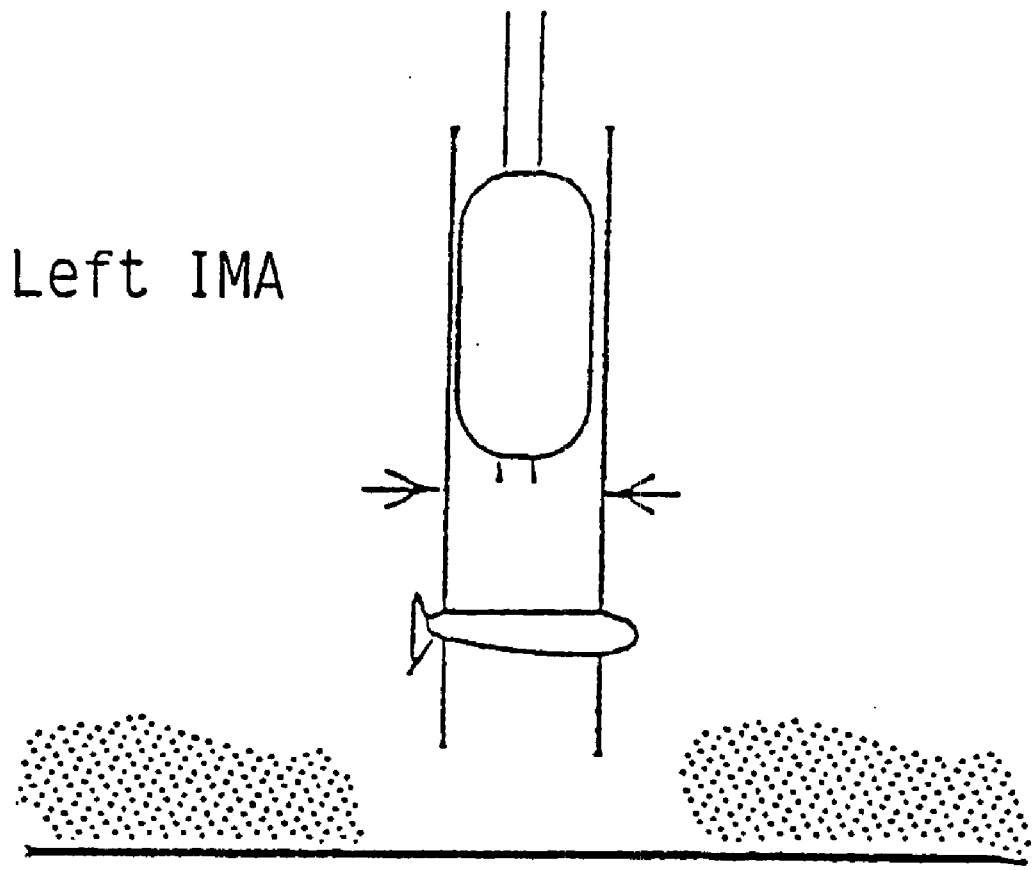
Figure 14:
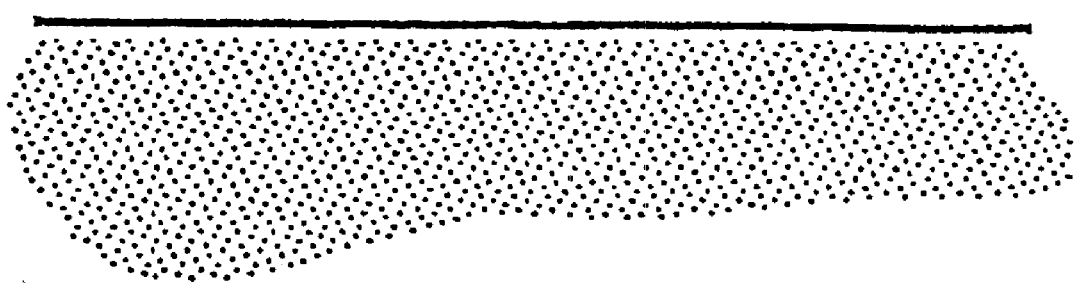
Figure 15:
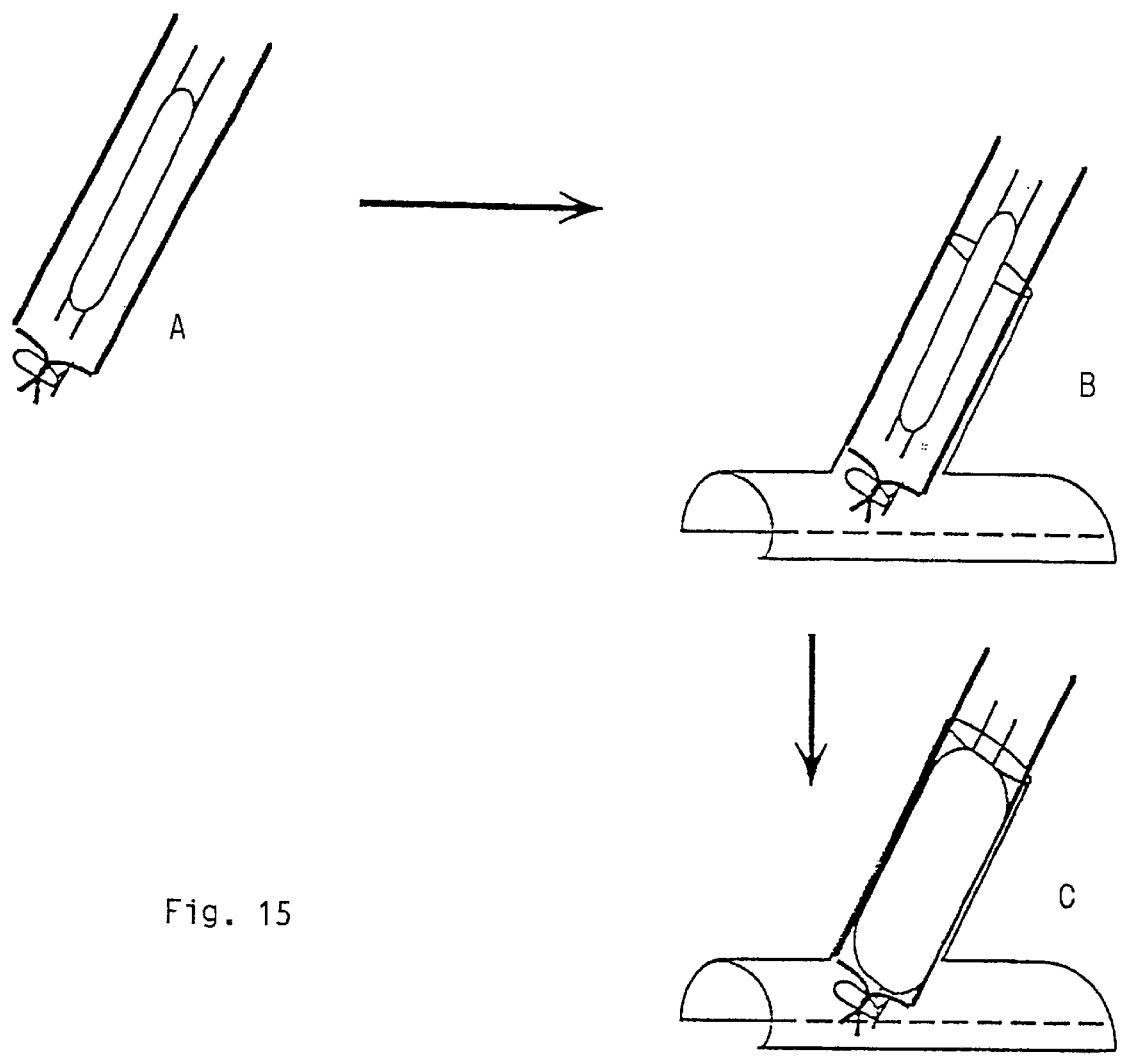
Figure 16:
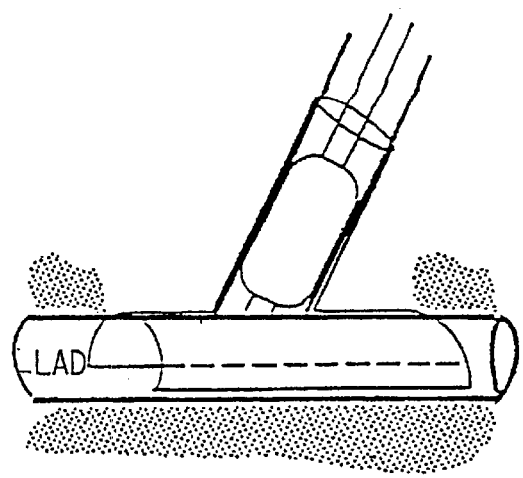
Figure 17:
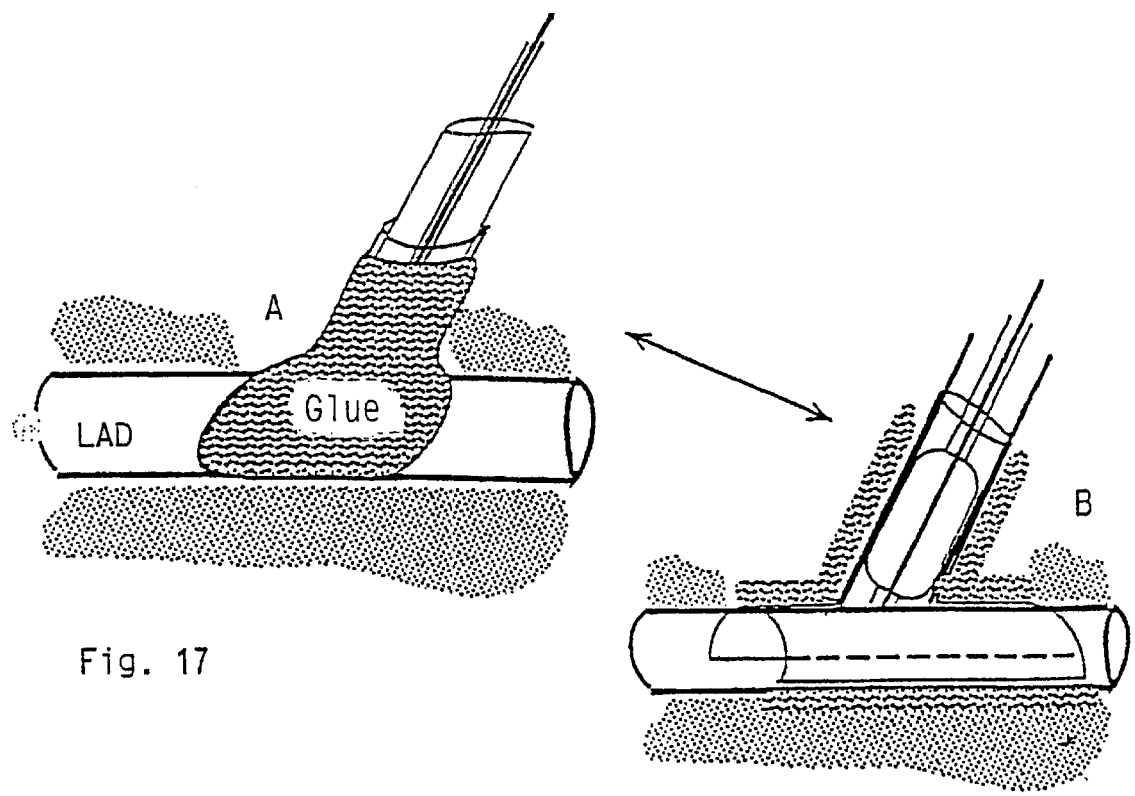
Figure 18:
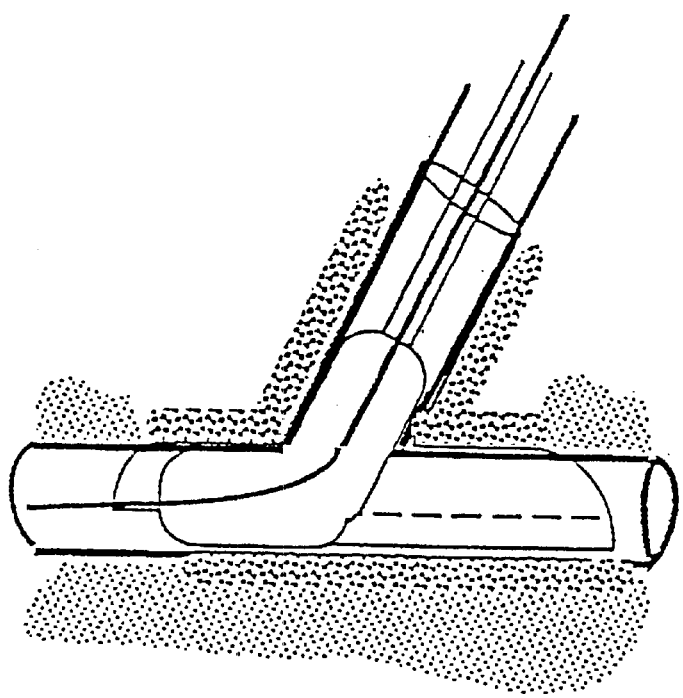
Figure 19:
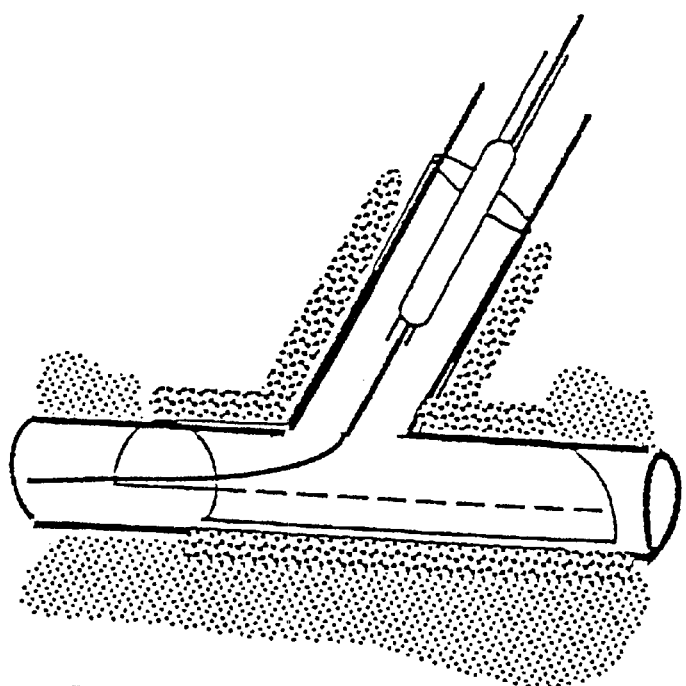
Figure 20:
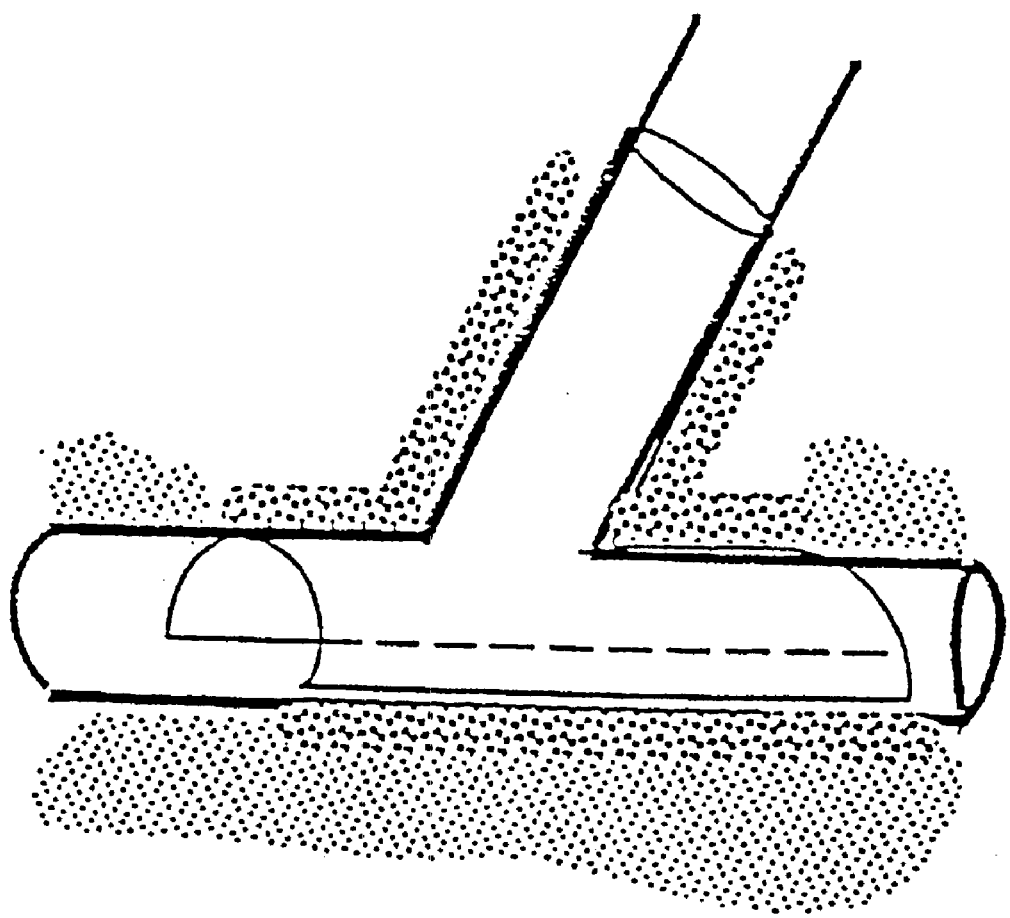

It is assumed that the device is precoated with an single component adhesive or the substrate of a two component adhesive. If the device is not precoated with a single component adhesive/substrate of two-component adhesive, it is applied to the inner surface of the anastomosis device before it is introduced into the operative field.
1. Angiography of left anterior descending artery (LAD) is performed to identify the best site for anastomosis, a skin marker is placed, and the catheter removed (FIG. 1)
2. Angiography of left internal mammary artery is performed to identify any anomaly that will hinder use of the vessel as a bypass, and the catheter is left in situ (FIG. 13)
3. Left IMA is endoscopically dissected (FIG. 14)
4. The angiography catheter in left IMA is exchanged for an angioplasty catheter.
5. The angioplastic catheter is advanced in left IMA until its tip is at the site selected for anastomosis, the balloon is inflated.
6. Two clip are placed on the vessel distal to the catheter tip, and the vessel divided in between, flush with catheter tip (FIG. 14).
7. Left anterior descending artery (LAD) is endoscopically dissected at the site selected for anastomosis (FIG. 2).
8. The stump ofleft IMA is held with a pair of forceps and drawn into the side-arm of a type I Y-shaped anastomosis device (FIGS. 1, 15A, 15B and 15C).
   (Modification: If a two component adhesive is being used, the appropriate activator is sprayed on the stump of left IMA.)
9. The balloon is inflated apposing the wall of left IMA to the inner surface of the anastomosis device (FIGS. 15A, 15B and 15C).
   (Modfication: If a photopolymerizable adhesive is being used, light of an appropriate wavelength is beamed on the side-arm of the anastomosis device.)
10. The balloon is deflated and the catheter withdrawn a short distance. The balloon is reinflated.
11. The stump of left IMA protruding from the sidearm of the anastomosis device distal to the catheter tip is cut flush with the inner surface of the anastomosis device.
12. The edges of the anastomosis device are distracted and the device is placed on the LAD. (FIG. 16).
    (Modifications:
      (i) If a two component adhesive is being used, the appropriate activator is sprayed on the surface of LAD prior to placement of the anastomosis device.)
      (ii) If a photoplymerizable adhesive is being used, light of an appropriate wavelength is beamed on the the anastomosis device after it is placed on LAD.
      (iii) If the anastomosis device is made of/reinforced with a thermodynamic alloy, physiologic saline at temperature higher than the TTR of the alloy is sprayed over the anastomosis device after it is placed on LAD.
      (iv) If a type Ib anastomosis device is being used, its flat component is tamped down over LAD and its surrounding tissues.)
13. More adhesive is sprayed along the edges of the anastomosis device, and on its surface (FIG. 17).
14. A guidewire or an optical fibre is passed through the angioplasty catheter.
15. Using radiofrequency alternating current carried by the guidewire or a laser beam, the outflow vessel is perforated (FIG. 18).
16. The balloon is deflated and the catheter is advanced, and the anastomosis dilated (FIG. 18).
17. The balloon is deflated and the catheter is withdrawn into the left IMA (FIG. 19).
18. The integrity of the anastomosis is endoscopically verified (FIG. 20).
19. The angioplasty catheter is replaced with a Doppler guidewire, and pressure gradient across the anastomosis is measured.
20. The Doppler guidewire is replaced with an angiography catheter or endosonography catheter and an endoluminal examination performed.
21. Depending on the findings, a spasmolytic, thrombolytic is administered, or the anastomosis redilated at higher pressures.

EXAMPLE 2

Figure 21:
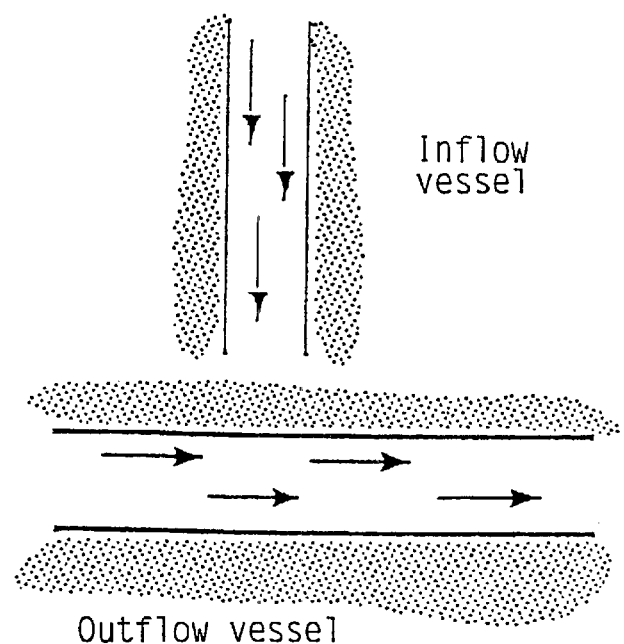
Figure 22:
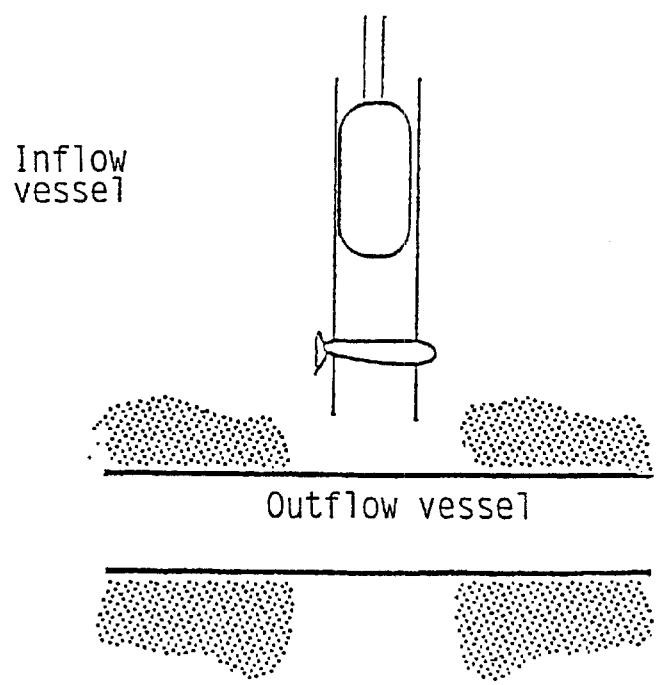
Figure 23:
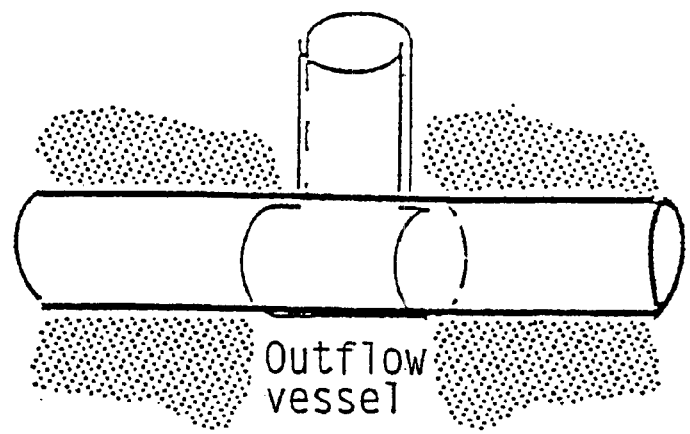

Externally Stented End-to-side Anastomosis with an Anastmosis Device (type I or II [Y-shaped])(FIGS. 1–13) Alone, for Outflow Vessels Which can be Circumferentially Dissected Steps 1–7 are as described above in Example 1 (FIG. 21).
8. The balloon is inflated and the stump of left IMA cut flush with the tip of the catheter (FIG. 22).
9. A type II Y-shaped anastomosis support device (FIG. 3) is slipped around the outflow vessel so that it fits snugly in the main stem of the support device (FIG. 23).

Figure 24A:
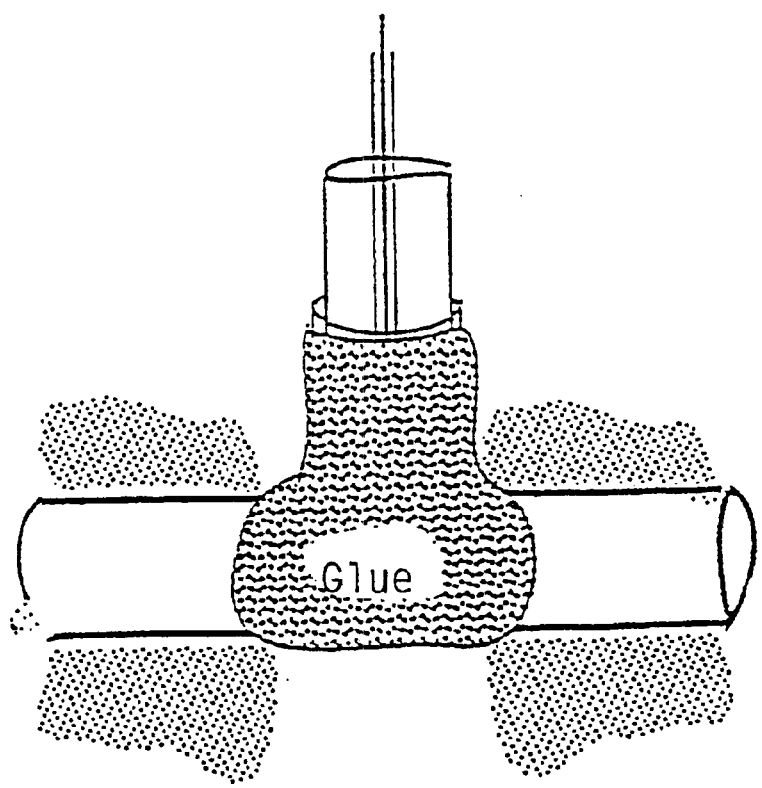
Figure 24B:
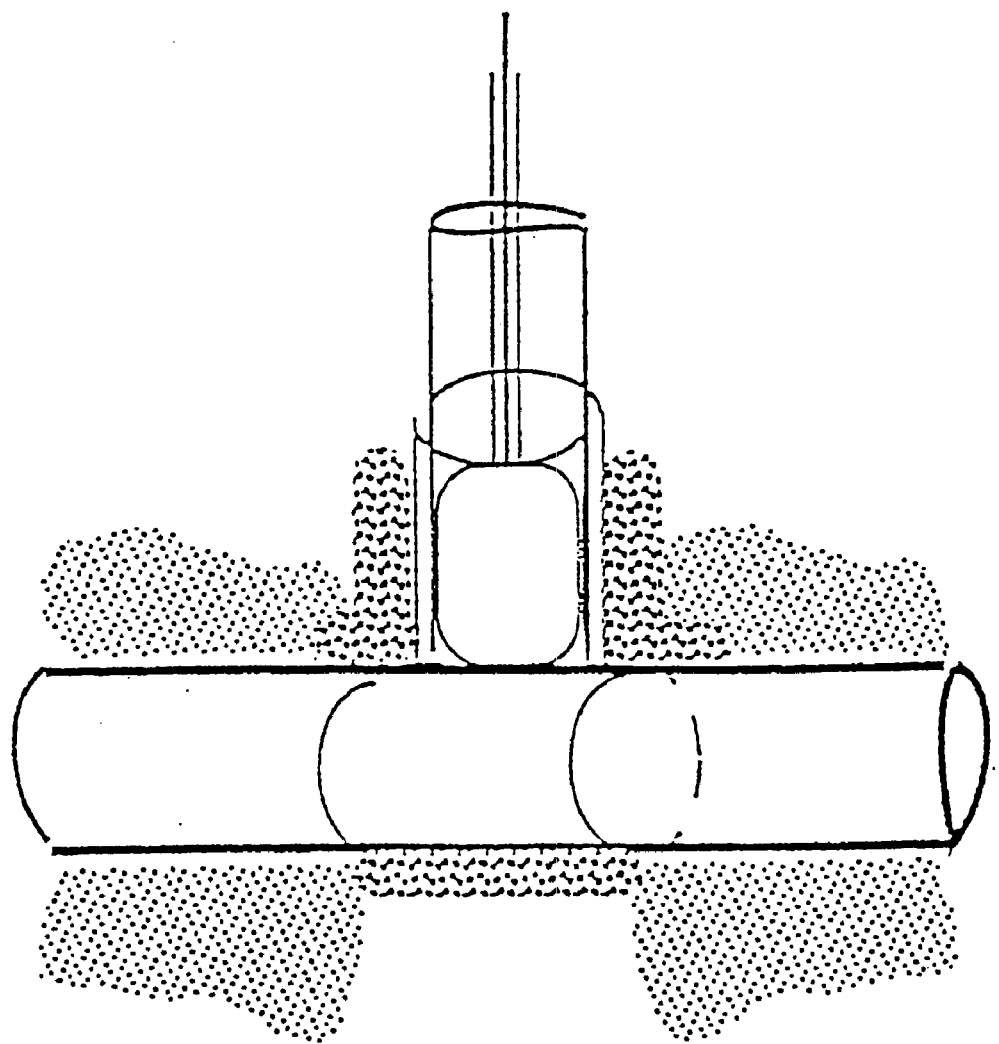

10. The stump of the outflow vessel is then placed in the side-arm of the support device so that it abuts the inflow vessel (FIG. 24A, 24B). The two halves of the anastomosis device are approximated and held thus for a few minutes.

(Modifications:
(i) If a two component adhesive is being used, the appropriate activator is sprayed on the surface of both outflow and inflow vessels prior to approximating edges of the anastomosis device.
(ii) If a photoplymerizable adhesive is being used, light of an appropriate wavelength is beamed on the the anastomosis device after the edges are approximated.
(iii) If the anastomosis device is made of/reinforced with a thermodynamic alloy, physiologic saline at temperature higher than the TTR of the alloy is sprayed over the anastomosis device after the inflow vessel is placed in the sidearm.
(iv) Radial compressive forces are applied to the anastomosis device if it is equipped with adhesive/fixation strips or a locking mechanism.)

The rest of the procedure comprises steps 13–20 described above (Example 1).

EXAMPLE 3

Externally Stented End-to-side Anastomosis with a Type III (Double-barrel) Anastomosis Device (FIG. 4) Alone The same procedure is used irrespective of whether the outflow vessel can be circumferentially dissected. The first four steps are the same as in Example 1.

Figure 25:
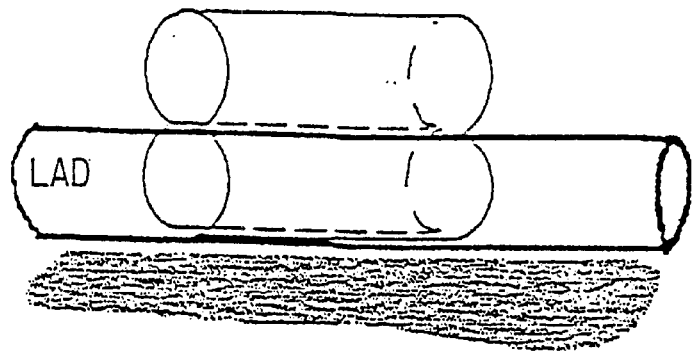
FIGS. 25–32 illustrate an externally stented end-to-side anastomosis by means of the device according to the invention.

5. The angioplasty catheter is advanced in left IMA until its tip is at the site selected for anastomosis. The vessel is ligated at two sites distal to the catheter tip, and the vessel divided in between.
6. LAD is endoscopically dissected at the site selected for anastomosis.
7. The free edges of the type III anastomosis device (FIG. C) are distracted and it is placed on the LAD (FIG. 25).

(Modifications:
(i) If a two component adhesive is being used, the appropriate activator is sprayed on the surface of LAD prior to placement of the anastomosis device.
(ii) If the anastomosis device is made of/reinforced with a thermodynamic alloy, physiologic saline at temperature higher than the TTR of the alloy is sprayed over the anastomosis device after it is placed on LAD.)
(iii) Radial compressive forces are applied to the anastomosis device if it is equipped with adhesive/fixation strips or a locking mechanism.)

Figure 26:
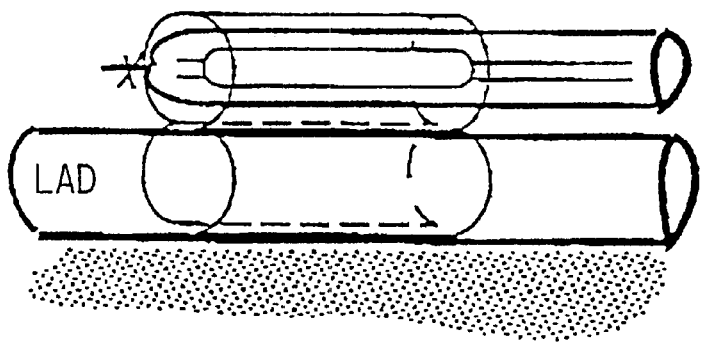

8. The ligated stump of left IMA is held with a pair of forceps and drawn into the vacant limb of the anastomosis device (FIG. 26).

(Modification:
(i) If a two component adhesive is being used, the appropriate activator is sprayed on the stump of left IMA.)

Figure 27:
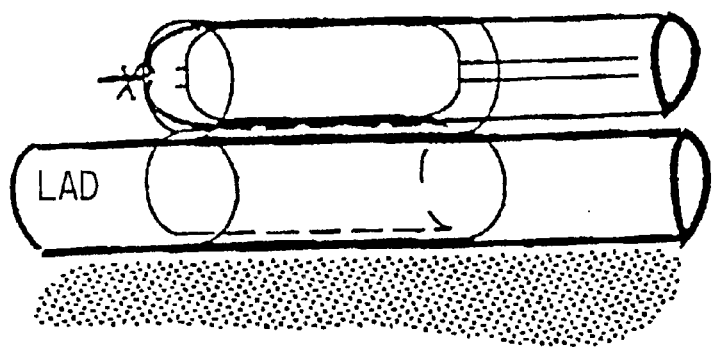

9. The balloon is inflated apposing the external surface of IMA with the external surface of LAD and the luminal surface of the anastomosis device, facilitating the formation of cohesive adhesive bonds between them (FIG. 27).

(Modfication:
(i) If a photopolymerizable adhesive is being used, light of an appropriate wavelength is beamed on the anastomosis device.

Figure 28A:
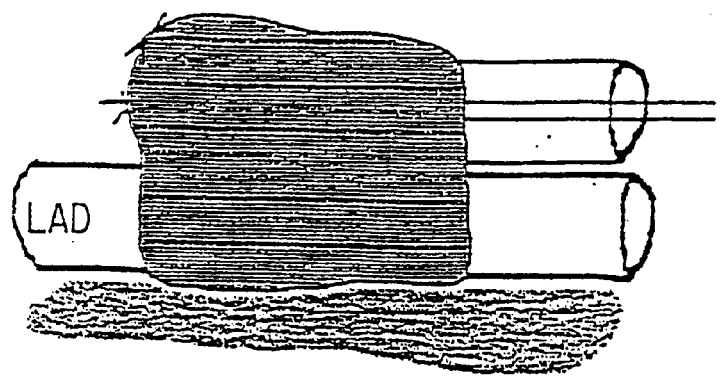
Figure 28B:
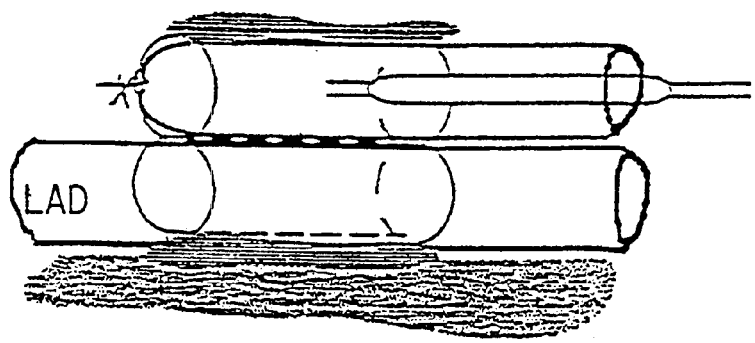

10. More adhesive is sprayed along the edges of the anastomosis device, and on its surface (FIGS. 28A and 28B).

Figure 29:
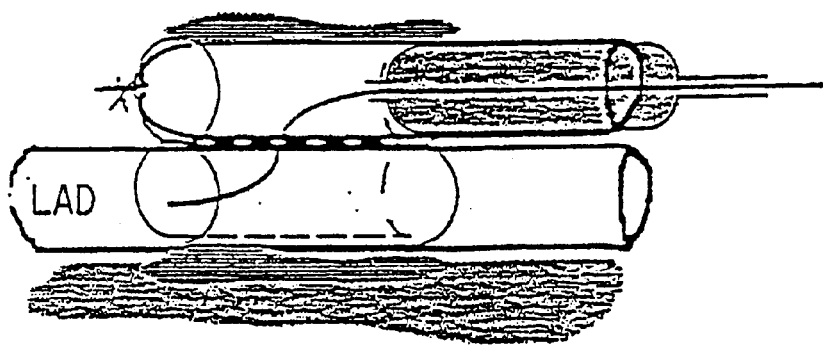
Figure 30:
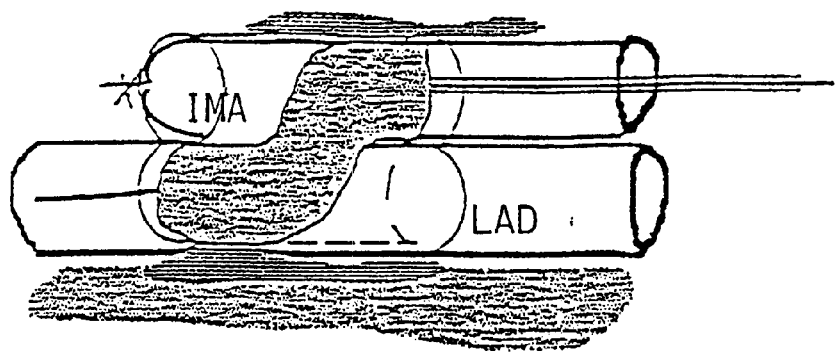

11. The balloon is deflated and the catheter is withdrawn a short distance. The balloon is inflated and a torque-controlled guidewire introduced through the catheter (FIG. 29).
12. Using radiofrequency alternating current carried by the guidewire, the adherent walls of IMA and LAD are perforated and the wire advanced to a secure position in the latter (FIG. 29).
13. The balloon catheter is advanced into LAD. The balloon is inflated to dilate the anastomosis. The balloon is deflated and the catheter is withdrawn into left IMA (FIG. 30).

Figure 31:
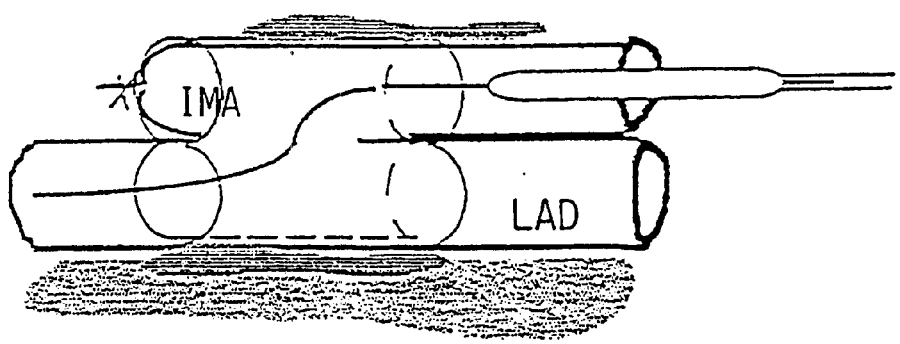
Figure 32:
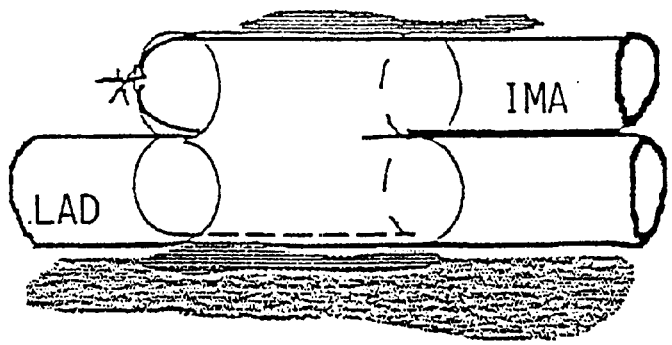

The rest of the procedure comprises of steps 13–20 described in example 1 (FIGS. 31, 32).

EXAMPLE 4

Externally Stented End-to-side Anastomosis with an IKF-IS Anastomosis Kit (FIGS. 1, 6A, 6B, 7A, 7B), for Outflow Vessels Which Cannot be Circumferentially Dissected (e.g. Left Anterior Descending Artery)

It is assumed that the components of the kit are precoated with an single component adhesive or the substrate of a two component adhesive. If they are not pre-coated with a single component adhesive/substrate of two component adhesive, it is applied before the various components of the anatomosis kit are introduced into the operative field.

Figure 33:
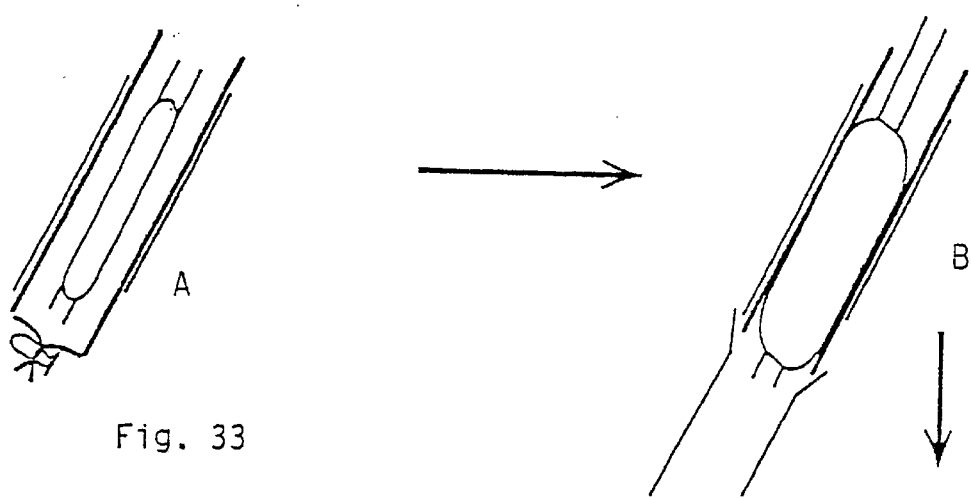
Figure 34:
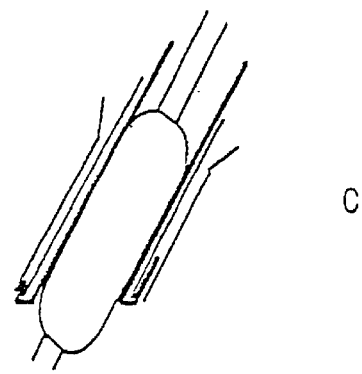
Figure 34:
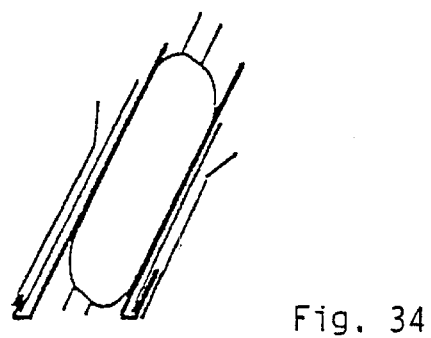

Steps 1–7 are as in Example 1.
8. The stump of left IMA is held with a pair of forceps and drawn into an inner sleeve (FIGS. 33A, 33B, 33C).
9. The balloon is inflated apposing the wall of left IMA to the inner surface of the inner sleeve (FIGS. 6A and 6B).
10. While the inner sleeve is held in position a fixation sleeve (FIGS. 7A, 7B) is drawn over it everting free edge of left IMA and fixing it to the outer surface of the inner sleeve (FIG. 34).

(Modifications:
(i) If a two-component adhesive is being used, activator is sprayed on the inner sleeve before the fixation sleeve is placed.
(ii) If the fixation sleeve is made of/reinforced with a thermodynamic alloy, physiologic saline at temperature higher than the TTR of the alloy is sprayed over the sleeve after it is drawn over the inner sleeve.
(iii) If the inner and fixation sleeves have metal collars, they are crimped securing the sleeves to each other.)

11. The fixation collar carrying the inflow vesssel is inserted into the sidearm of a type I anastomosis device (FIG. 36).

(Modfications:
(i) If a two-component adhesive is being used, activator is sprayed on the fixation sleeve before it is placed in the side-arm.
(ii) If a photopolymerizable adhesive is being used, light of the appropriate wavelength is beamed on the sidearm.
(iii) If the the fixation sleeve and the side-arm of the anastomosis device have metal collars, they are crimped securing the sleeves to each other.)

Figure 35:
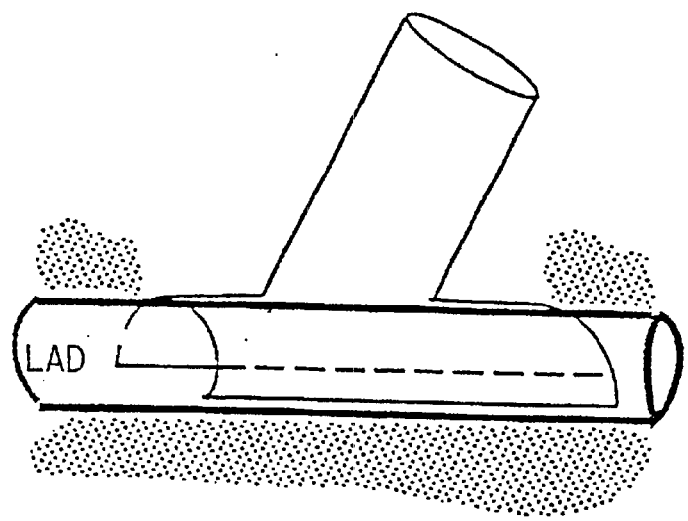
Figures 37A, 37B:
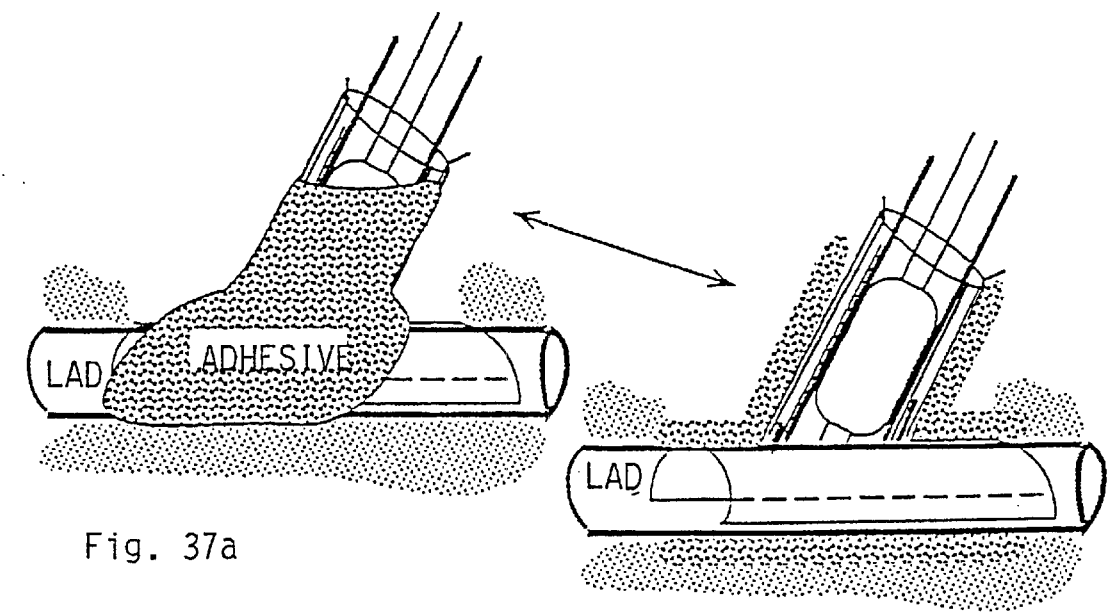

The rest of the procedure comprises steps 13–20 described under example 1 (FIGS. 35, 37A, 37B).

EXAMPLE 5

Figure 38:
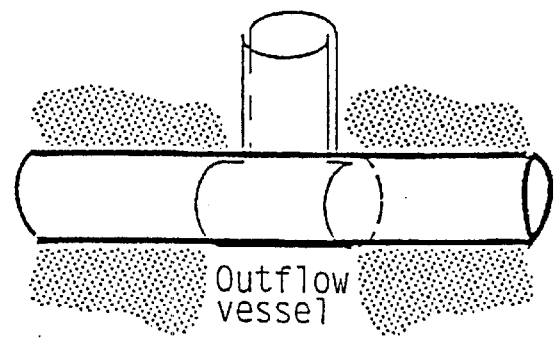

Externally Stented End-to-side Anastomosis with an IKF-IS Anastomosis Kit (FIGS. 3, 6A, 6B, 7A, 7B), for Outflow Vessels Which can be Circumferentially Dissected Steps 1–10 are the same as for example 4.
11. A type II anastomosis device is slipped around the outflow vessel so that it lies snugly in the stem of the anastomosis device (FIG. 38).

Figures 39A, 39B:
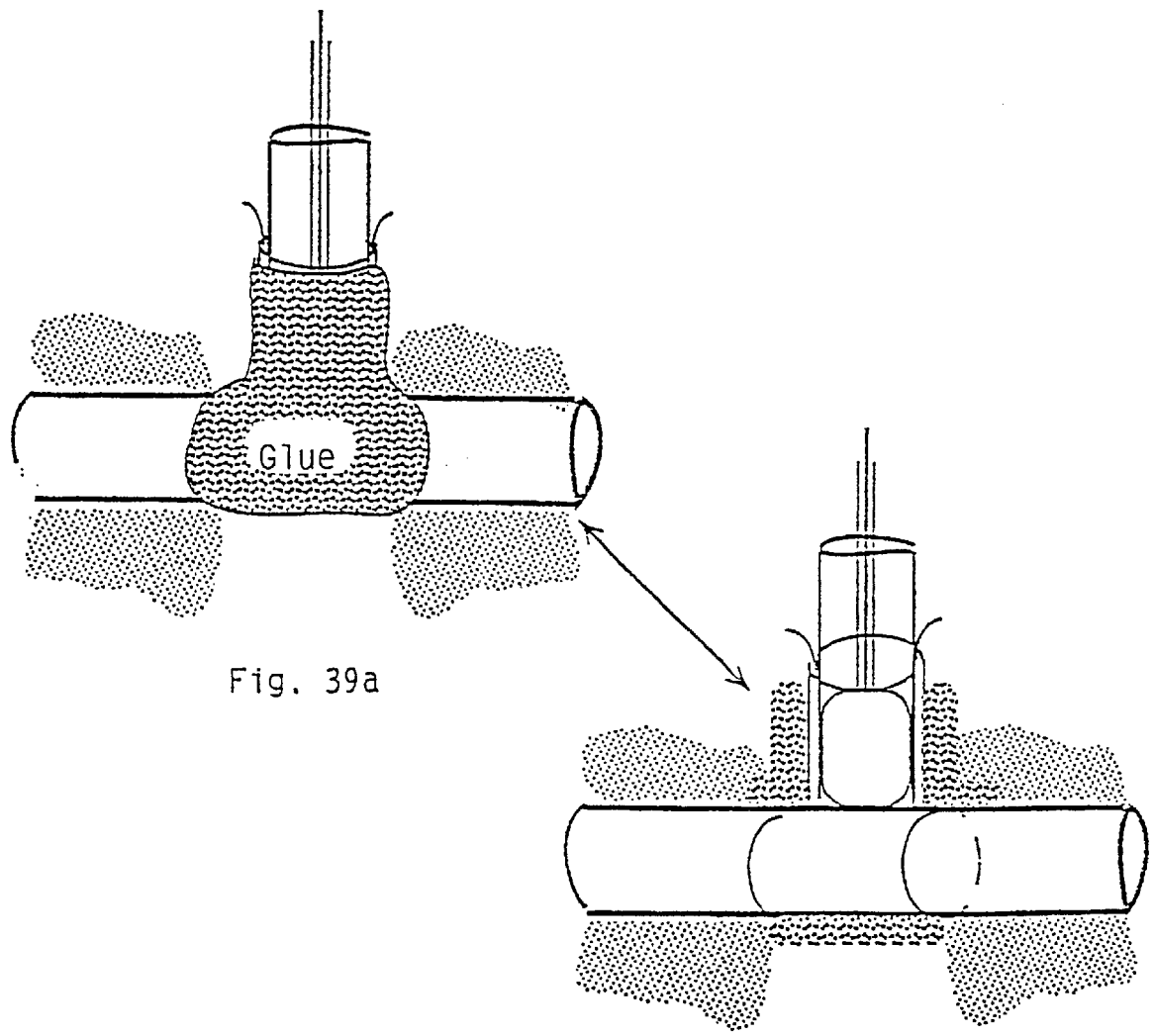

12. The fixation sleeve carrying the inflow vessel is then placed in the sidearm of the anastomosis device such that it abuts the outflow vessel. The two halves of the anastomosis device are approximated and held thus for a few minutes (FIGS. 39A, 39B).

(Modifications:
- (i) If a two component adhesive is being used, the appropriate activator is sprayed on the surface of both outflow and inflow vessels prior to approximating edges of the anastomosis device.
- (ii) If a photoplymerizable adhesive is being used, light of an appropriate wavelength is beamed on the the anastomosis device after the edges are approximated.
- (iii) If the anastomosis device is made of/reinforced with a thermodynamic alloy, physiologic saline at temperature higher than the TTR of the alloy is sprayed over the anastomosis device after the inflow vessel is placed in the sidearm.
- (iv) Radial compressive forces are applied to the anastomosis device if it is equipped with adhesive/fixation strips or a locking mechanism).

The rest of the procedure comprises steps 13–20 of Example 1.

EXAMPLE 6

Externally Stented End-to-end Anastomosis

It is assumed that the anastomosis device/components of anatomosis kit are precoated with an single component adhesive or the substrate of a two component adhesive. If the device is not pre-coated with a single component adhesive/substrate of two-component adhesive, it is applied to the inner surface of the anastomosis device before it is introduced into the operative field.

Figure 40:
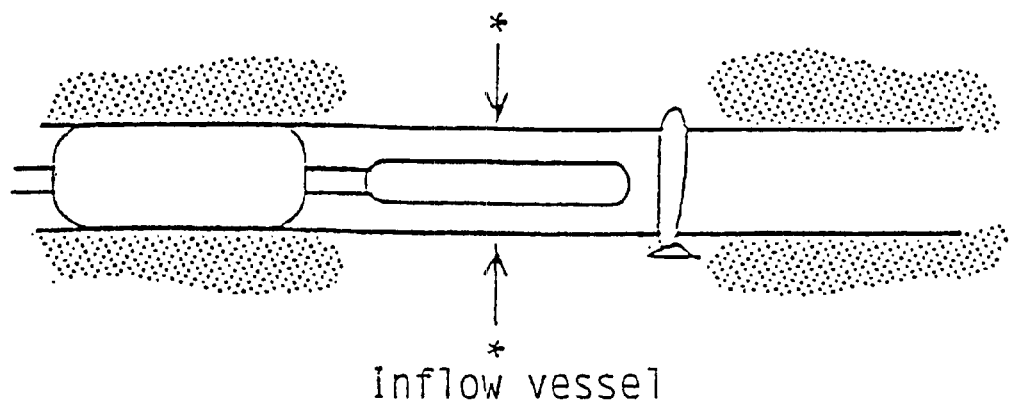
FIGS. 40–46 illustrate an externally stented end-to-end anastomosis by means of the device according to the invention.
Figure 41:
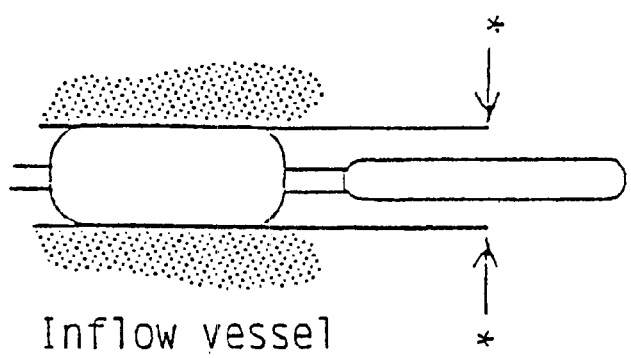
Figure 42:
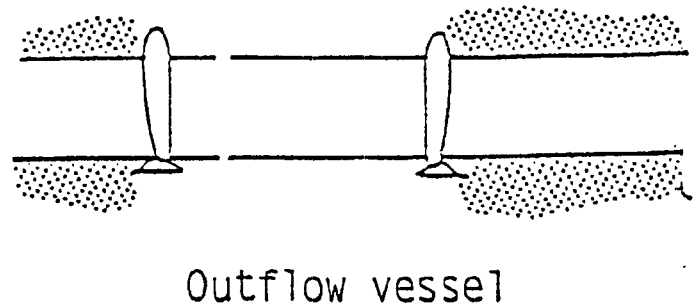
Figure 43:
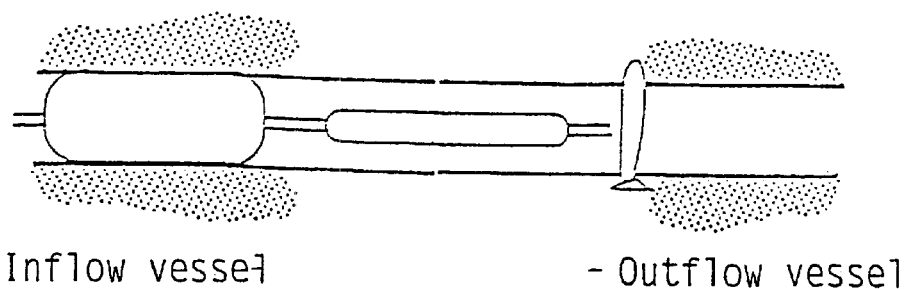
Figure 44:
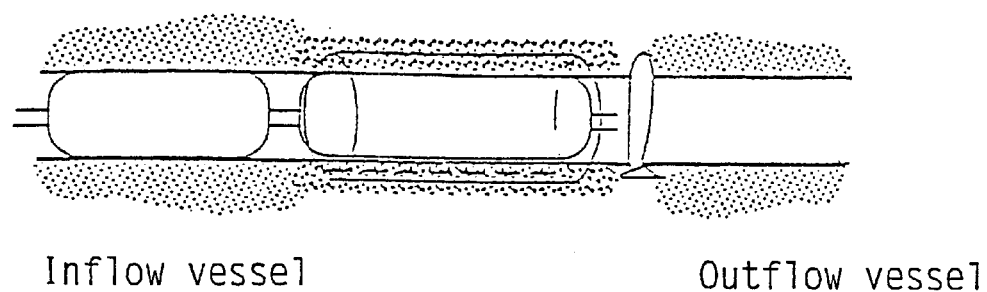

1. Angiography of the outflow vessel is performed to identify the best site for anastomosis, skin marker placed, and catheter is removed.
2. Angiography of the inflow vessel is performed to identify any anomaly that will hinder use of the vessel as a bypass.
3. The inflow vessel is endoscopically dissected.
4. The angiography catheter is exchanged for a triple-lumen, double-balloon catheter which is advanced till its distal balloon lies astride the site selected for anastomosis. The balloon is inflated and its midpoint marked on the adventitia. A clip is placed on the vessel distal to the balloon (FIG. 40).
5. The proximal balloon is inflated and the distal balloon deflated. The vessel is divided at the site marked on the adventitia (FIG. 41).
6. The outflow vessel is endoscopically dissected and a clip placed on each side of the site selected for anastomosis. The vessel is divided between the clips (FIG. 42).
7. The inflow and outflow vessels are aligned along a common longitudinal axis (FIG. 43).
8. The balloon catheter is introduced into the lumen of the outflow vessel and advanced until the divided edges of the two vessels abut against each other (FIG. 43). The distal balloon is inflated.
9. The anastomosis device is slipped around the vessels and gently tamped against the inflated balloon (FIG. 44).

(Modifications:
- (i) If a two component adhesive is being used, the appropriate activator is sprayed on the surface of the outflow and inflow vessels prior to placement of the anastomosis device.
- (ii) If a photoplymerizable adhesive is being used, light of an appropriate wavelength is beamed on the anastomosis device after placement.
- (iii) If the anastomosis device is made of/reinforced with a thermodynamic alloy, physiologic saline at temperature higher than the TTR of the alloy is sprayed over the anastomosis device after it is placed.
- (iv) Radial compressive forces are applied to the anastomosis device if it is equipped with adhesive/fixation strips or a locking mechanism).

Figure 45:
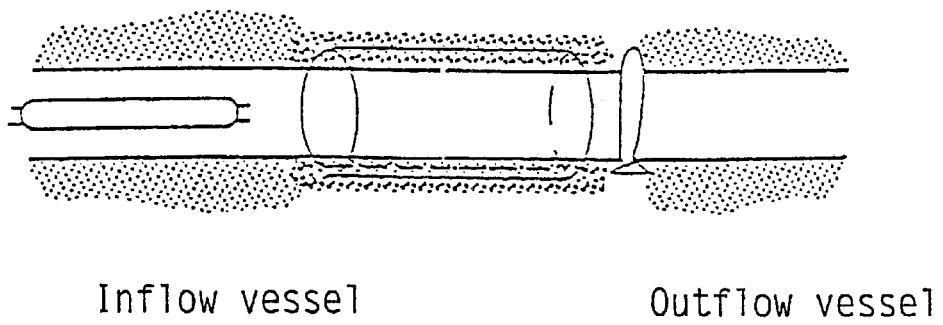
Figure 46:
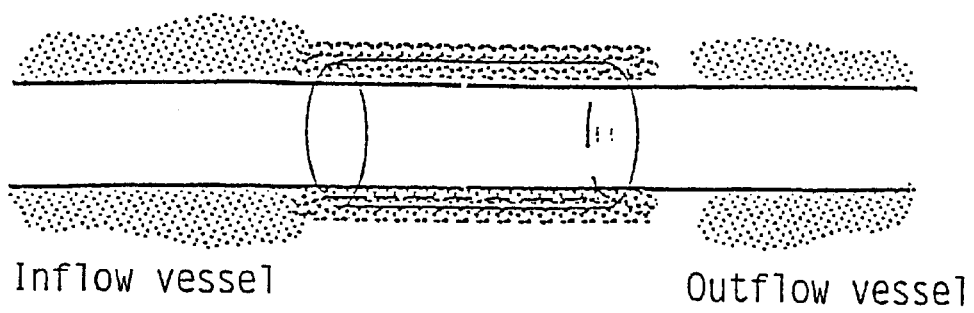

10. More adhesive is sprayed along the seam of the anastomosis device and its edges and on its surface (FIG. 45).
11. Both balloons are deflated and the catheter withdrawn proximal to the anastomosis (FIG. 45). The integrity of the anastomosis is endcoscopically verified (FIG. 46). If deemed necessary the pressure gradient across the anastomosis is measured followed by sonographic or radiographic examination. Depending on the findings, a spasmolytic or thrombolytic will be administered.

Based on the creation of a suturless anastomosis under videoendoscopic-radiographic guidance, the IKF-IS technique represents an original concept that has this far not been investigated. If the underlying hypothesis proves to be right, it could be the first procedure in a whole new family of minimally invasive reconstructive procedures that could be used in coronary circulation areas, in other vascular areas of the body and also at extravascular locations such as the oesophagus, intestines, ureter, biliary ducts and fallopian tubes.

About 900–1000 percutaneous coronary angioplasties per million inhabitants are performed annually in North America and Western Europe. Approximately half of these are related to a diseased left anterior descending artery and can be treated by means of the IKF-IS technique. The IKF-IS procedure can also be a substitute for coronary bypass grafting (300.000 procedures/year in the US) when the culprit lesion lies in the left anterior descending artery. In addition a substantial number of patients with multivessel disease can also benefit because the IKF-IS technique being radiographically guided can be easily combined with percutaneous angioplasty.

The above mentioned IKF-IS technique offers a simple, inexpensive option that can be used with endoscopic-fluoroscopic guidance. Antegrade flow in the outflow vessel will be stopped for only a few seconds, reducing the possibility of ischaemic complications. Restrain of the cardiac motion at the anastomosis is unnecessary, and thus expensive custom-made instruments or creation of cardioplegia and cardiopulmonary bypass are avoided.

Ostial stenosis reported as a consequence of use of laser in e.g. the Tulleken technique may not represent a problem because the anastomosis is created by means of pneumatic dilation.

There is a clear need in the market for devices according to the invention that make performance of suturless anastomosis in a safe and inexpensive way possible.

What is claimed is:

1. A device for endoscopic suturless anastomosis of tubular organs selected from the group comprising blood vessels and extravascular tubular structures such as the esophagus, intestines, ureter, biliary ducts, fallopian tubes, etc., said device comprising a first curved member and one or several second tubular members, wherein the first curved member is a first tubular member provided with an opening for communication with the second tubular member, and a slit which extends longitudinally throughout the whole length of the first curved member, for placement of the device externally to said organs, such that the anastomosis is externally supported by the device;

inner surfaces of the first and the second members are in continuity, such that the size of the opening on the side of the first member is substantially equal to a luminal area of the second members; and inner and outer diameters of any radial cross section of the second member are constant along the length of the second member.

2. The anastomosis device according to claim 1, wherein an inner surface of the device is lined with an appropriate adhesive.

3. The anastomosis device according to claim 1, wherein the second tubular member is on one or both sides provided with a collar of thermodynamic shape memory metal or polymer.

4. The anastomosis device according to claim 1, wherein the second tubular member is arranged on an area of the first tubular member opposite the slit.

5. The anastomosis device according to claim 4, wherein the second tubular member is provided with a slit.

6. The anastomosis device according to claim 5, wherein the slits in the first and second tubular members are in correspondence.

7. The anastomosis device according to claim 1, wherein the first and second tubular members are parallel.

8. The anastomosis device according to claim 1, wherein the one or more additional tubular members coaxially fit within the second tubular member of the anastomosis device in telescopic fashion, and that leading edges of these tubular members and the edge of the second tubular member in contact with the first curved member are provided with biocompatible metal collars, wherein, the innermost metal collar is most resistant to physical deformation.

9. The anastomosis device according to claim 1, wherein the slits have edges that are configured to mechanically lock on the application of a radial force, e.g. with a Z-profile.

10. The anastomosis device according to claim 1, wherein the slits have edges that form overlapping flaps and that the surfaces of the flaps facing each other are provided with a fastening material, e.g. Velcro.

11. The anastomosis device according to claim 1, wherein the device is provided along its free edges with a continuous strip of a thermodynamic shape-memory metal with transitional temperature range above normal body temperature.

12. The anastomosis device according to claim 1, wherein the device is reinforced with a mobile, coaxial, close-fitting collar that will be drawn over the device to secure its closure.

* * * * *